(12) United States Patent
Stemniski et al.

(10) Patent No.: US 10,413,308 B2
(45) Date of Patent: Sep. 17, 2019

(54) PATIENT-SPECIFIC SURGICAL DEVICES, SYSTEMS, AND METHODS

(71) Applicant: Wright Medical Technology, Inc., Memphis, TN (US)

(72) Inventors: Paul M. Stemniski, Arlington, TN (US); David G. Reynolds, Fairport, NY (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 14/442,595

(22) PCT Filed: Mar. 13, 2015

(86) PCT No.: PCT/US2015/020414
§ 371 (c)(1),
(2) Date: May 13, 2015

(87) PCT Pub. No.: WO2016/148675
PCT Pub. Date: Sep. 22, 2016

(65) Prior Publication Data
US 2018/0177513 A1    Jun. 28, 2018

(51) Int. Cl.
*A61B 17/17* (2006.01)
*A61B 17/15* (2006.01)
(Continued)

(52) U.S. Cl.
CPC .......... *A61B 17/1775* (2016.11); *A61B 17/15* (2013.01); *A61B 17/1796* (2013.01); *A61B 2017/568* (2013.01); *A61B 2090/3966* (2016.02)

(58) Field of Classification Search
CPC ............ A61B 17/1742; A61B 17/1764; A61B 17/1778; A61B 17/1782; A61B 17/1739;
(Continued)

(56) References Cited

U.S. PATENT DOCUMENTS

| 5,423,827 A | 6/1995 | Mumme et al. |
| 5,768,134 A | 6/1998 | Swaelens et al. |

(Continued)

FOREIGN PATENT DOCUMENTS

| CA | 2836651 | 6/2014 |
| CN | 102458269 A | 5/2012 |

(Continued)

OTHER PUBLICATIONS

Examination Report issued in corresponding Australian patent application No. 2015202252, dated May 11, 2016, 6 pages.
(Continued)

*Primary Examiner* — Zade Coley
*Assistant Examiner* — Jessica Weiss
(74) *Attorney, Agent, or Firm* — Duane Morris LLP

(57) ABSTRACT

A surgical device includes a body having a first side with a first surface that is complementary to a surface of a foreign object disposed within a patient based on preoperative imaging of the patient. The body defines at least one hole positioned relative to the body to facilitate insertion of an elongate device at a predetermined location relative to the foreign object.

16 Claims, 10 Drawing Sheets

(51) Int. Cl.
*A61B 90/00* (2016.01)
*A61B 17/56* (2006.01)

(58) Field of Classification Search
CPC ............ A61B 17/1775; A61B 17/1796; A61B 2090/3966; A61B 2017/568
USPC ...................................................... 606/96–98
See application file for complete search history.

(56) References Cited

U.S. PATENT DOCUMENTS

| | | | |
|---|---|---|---|
| 8,337,503 | B2 | 12/2012 | Lian |
| 8,377,066 | B2 * | 2/2013 | Katrana ................. A61B 17/15 606/86 R |
| 8,808,297 | B2 | 8/2014 | Stemniski et al. |
| 8,808,303 | B2 | 8/2014 | Stemniski et al. |
| 9,017,334 | B2 | 4/2015 | Carroll et al. |
| 2010/0212138 | A1 | 8/2010 | Carroll et al. |
| 2010/0217338 | A1 | 8/2010 | Carroll et al. |
| 2010/0262150 | A1 * | 10/2010 | Lian ........................ A61B 17/15 606/87 |
| 2011/0015636 | A1 * | 1/2011 | Katrana ................. A61B 17/15 606/87 |
| 2011/0319745 | A1 | 12/2011 | Frey |
| 2012/0123420 | A1 | 5/2012 | Honiball |
| 2012/0130434 | A1 | 5/2012 | Steminski |
| 2012/0239045 | A1 * | 9/2012 | Li ........................... A61B 17/15 606/88 |
| 2014/0163563 | A1 | 6/2014 | Reynolds et al. |
| 2014/0163570 | A1 | 6/2014 | Reynolds et al. |
| 2014/0257309 | A1 * | 9/2014 | Aram ..................... A61B 17/154 606/88 |
| 2014/0336658 | A1 | 11/2014 | Luna et al. |
| 2016/0296240 | A1 | 10/2016 | Schuster |

FOREIGN PATENT DOCUMENTS

| | | |
|---|---|---|
| CN | 103096819 A | 5/2013 |
| CN | 103841924 A | 6/2014 |
| CN | 103860244 A | 6/2014 |
| EP | 2742878 A1 | 6/2014 |
| JP | 2014-131724 A | 7/2014 |
| JP | 2014-531920 A | 12/2014 |
| WO | 2009045960 A1 | 4/2009 |
| WO | 2011018458 A1 | 2/2011 |
| WO | 2012024306 A2 | 2/2012 |
| WO | 2013/025814 A1 | 2/2013 |
| WO | 2013025814 A1 | 2/2013 |
| WO | 2013169475 A1 | 11/2013 |
| WO | 2014-026084 A1 | 2/2014 |
| WO | 2014020561 A | 2/2014 |
| WO | 2014020561 A1 | 2/2014 |

OTHER PUBLICATIONS

Office Action issued in connection with corresponding Canadian patent application No. 2,896,958, dated May 25, 2016, 4 pages.
Web Site: Total Ankle Institute, "Prophecy Inbone", Nov. 1, 2014 (tracked by waybackmachine) http://www.totalankleinstitute.com/INBONE/-Products/PROPHECY-INBONE) 5 pages.
International Search Report and Written Opinion of the International Searching Authority issued in connection with International Patent Application No. PCT/US2015/020414, 12 pages.
First Office Action issued for corresponding Japanese patent application No. 2016-544422, dated May 16, 2017, 3 pages.
Examination Report issued in corresponding Australian Patent Application No. 2017221820, dated Sep. 13, 2018, 4 pages.
Office Action issued in corresponding Chinese Patent Application No. 201580001470.2, dated Jul. 30, 2018, 8 pages.
Supplementary Partial European Search Report issued in corresponding European Patent Application No. 15721110, dated Mar. 19, 2019, 10 pages.
Second Office Action issued in corresponding Chinese Patent Application No. 201580001470.2, dated Jun. 4, 2019, 9 pages.

* cited by examiner

PATIENT-SPECIFIC SURGICAL DEVICES, SYSTEMS, AND METHODS

CROSS-REFERENCE TO RELATED APPLICATIONS

The present application is a U.S. national stage application under 35 U.S.C. § 371 of International Application No. PCT/US2015/020414, filed Mar. 13, 2015, the entirety of which is incorporated herein by reference.

FIELD OF DISCLOSURE

The disclosed systems and methods relate generally to surgical guides and fixtures to locate cutting guides during orthopedic procedures.

BACKGROUND

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint, i.e., an ankle, knee, shoulder, elbow, and hip, the misalignment could result in discomfort to the patient, gait problems, or degradation of the prosthesis. Over a period of time, the prosthesis may need to be replaced during what is known as a revision surgery.

Many surgical procedures, including revision procedures, employ the use of intra-operative fluoroscopy to check the alignment of the intramedullary cavities that are prepared to receive the joint replacement prosthesis. However, the use of intra-operative fluoroscopy in the operating room has several drawbacks. One such drawback is that the use of fluoroscopy to check the alignment of intramedullary cavities formed during surgery increases the overall length of the surgical procedure as time is taken to acquire and evaluate the fluoroscopic images. Long surgery times lead to increased tourniquet time for the patient and therefore may increase recovery time.

Another drawback of fluoroscopy is exposing the patient and others in the operating room to the ionizing radiation. For example, the U.S. Food and Drug Administration ("FDA") has issued several articles and public health advisories concerning the use of the fluoroscopy during surgical procedures. Consequently, even though steps are taken to protect the patient and other from the ionizing radiation, it is virtually impossible to eliminate all risk associated with the ionizing radiation.

SUMMARY

In some embodiments, a surgical device includes a body having a first side having a first surface that is complementary to a surface of a foreign object disposed within a patient based on preoperative imaging of the patient. The body defines at least one hole positioned relative to the body to facilitate insertion of an elongate device at a predetermined location relative to the foreign object.

In some embodiments, a system includes a surgical locator device and a first guide. The surgical locator device including a body having a first side and a second side. The first side of the surgical locator device including a first surface that is complementary to a surface of a foreign object disposed within a patient based on preoperative imaging of the patient. The body defines at least one hole positioned relative to the body to facilitate insertion of a first elongate device at a predetermined location relative to the foreign object. The first cutting guide defines at least one second hole sized and configured to receive the first elongate device therein for locating the first guide relative to the foreign object.

In some embodiments, a method includes establishing access to a joint of a patient and placing a surgical locator device in contact with the joint such that a first surface of the surgical locator device contact at least a portion of a foreign object disposed within the patient. The first surface of the surgical locator device is complementary to the portion of the foreign object based on preoperative imaging of the patient.

BRIEF DESCRIPTION OF THE DRAWINGS

These and other features and advantages of the disclosed systems and methods will be more fully disclosed in, or rendered obvious by, the following detailed description of the preferred embodiment of the disclosed systems and methods, which are to be considered together with the accompanying drawings wherein like numbers refer to like parts and further wherein.

DETAILED DESCRIPTION

Figure 1:
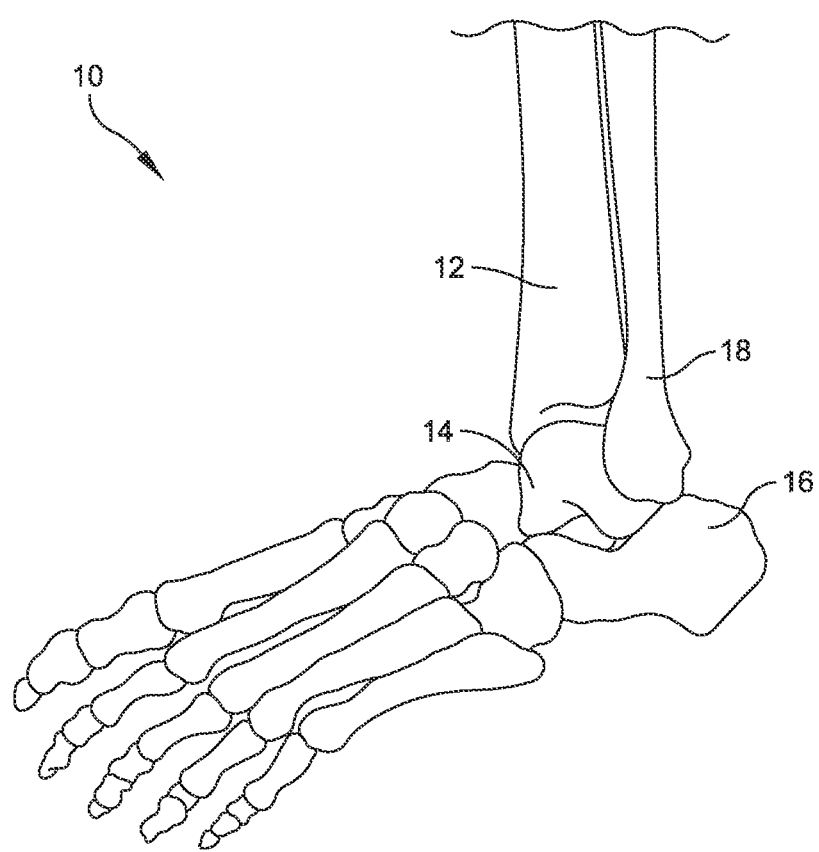
FIG. 1 illustrates one example of a human ankle and foot.

This description of embodiments is intended to be read in connection with the accompanying drawings, which are to be considered part of the entire written description of the disclosed systems and methods. The drawing figures are not necessarily to scale and certain features of the systems and methods may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods utilize custom manufactured surgical instruments, guides, and fixtures that are based upon a patient's anatomy as determined by a computer tomography scanner (CT), magnetic resonance imaging machine (MRI), or other medical imaging technology. These disclosed systems are derived from image data acquired through the medical imaging as taught by the systems and methods disclosed in U.S. Pat. No. 5,768,134 issued to Swaelens et al., commonly assigned U.S. patent application Ser. No. 12/710,898, entitled "Patient Specific Surgical Guide Locator and Mount," and commonly assigned U.S. patent application Ser. No. 12/711,307, entitled "Method for Forming a Patient Specific Surgical Guide Mount," the entirety of which are all incorporated by reference herein.

The disclosed systems and methods build on these disclosed systems and methods to provide the ability to perform surgical procedures beyond the initial installation of an orthopedic prosthesis. In some embodiments, the disclosed systems and methods are used to perform revision surgeries and/or fusion take-down surgeries. For example, the disclosed systems and methods utilize the imaging of one or more foreign objects in patient's body, such as a previously installed implant (including plates and screws, to list only a few possibilities), bone cement, bone graft, and/or other object not native to the patient's body, and creates surgical tools having a surface that conforms to and is complementary to a bone or cartilaginous surface and/or a surface of the one or more foreign objects. These disclosed systems and methods advantageously improve the accuracy of performing revision and other orthopedic procedures.

FIG. 1 illustrates one example of a patient's ankle joint 10 comprising a tibia 12, a talus 14, a calcaneus 16, and a fibula 18. The ankle joint 10 illustrated in FIG. 1 also includes a foreign object 50 disposed between tibia 12 and talus 14. While foreign object 50 is illustrated as bone cement, foreign object 50 can take the form of bone graft or a previously installed orthopedic implant. For example, in some embodiments, foreign object 50 includes one or more of a tibial component, talar component, stem component, plate, screw, or other component of an orthopedic prosthesis. Further, while the foreign object 50 is described as being positioned within an ankle joint 10, one of ordinary skill in the art will understand that the foreign object can be located in another joint including, but not limited to, a hip, knee, shoulder, elbow, and wrist, to identify only a few possible joints.

In some embodiments, ankle joint 10, or the joint of interest, including foreign object 50 is imaged using a medical imaging technology including, but not limited to, CT and MRI, to identify only a couple of possible technologies. The obtained image data is converted to a 3D model of the ankle 10, including foreign object 50, in accordance with the methods disclosed in, for example, U.S. Pat. No. 5,768,134 issued to Swaelens et al., commonly assigned U.S. patent application Ser. No. 12/710,898, entitled "Patient Specific Surgical Guide Locator and Mount," and commonly assigned U.S. patent application Ser. No. 12/711,307, entitled "Method for Forming a Patient Specific Surgical Guide Mount," all of which are incorporated by reference in their entireties.

Figure 2:
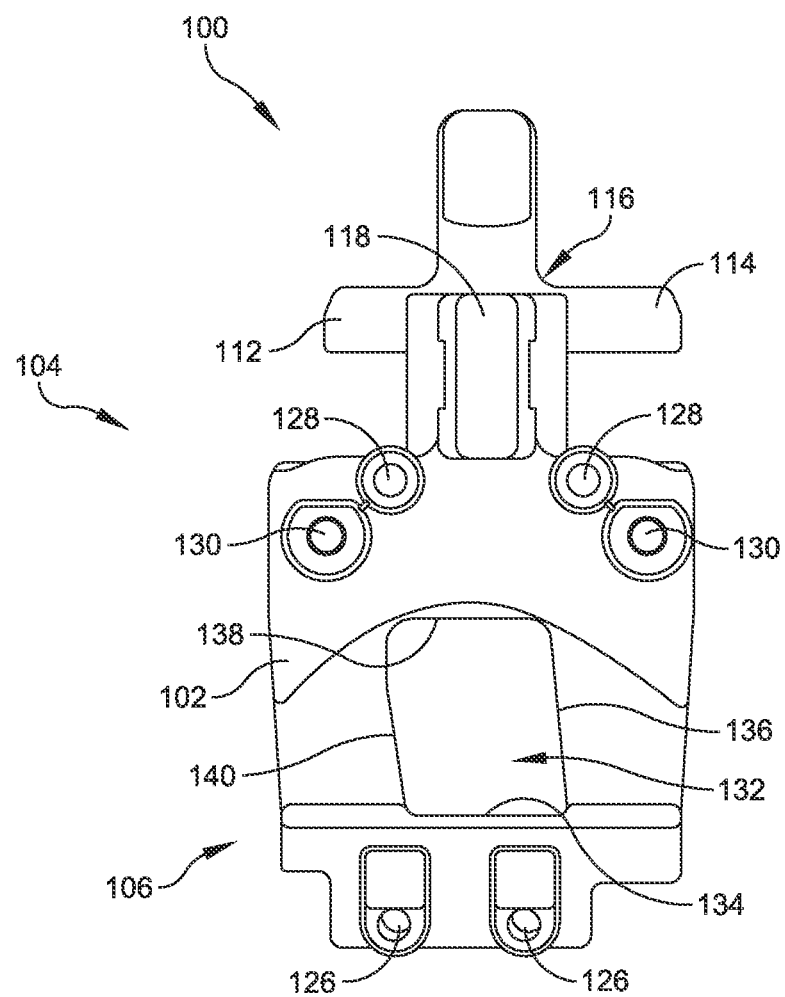
FIG. 2 is a plan view of one example of a surgical locator device in accordance with some embodiments.
Figure 3:
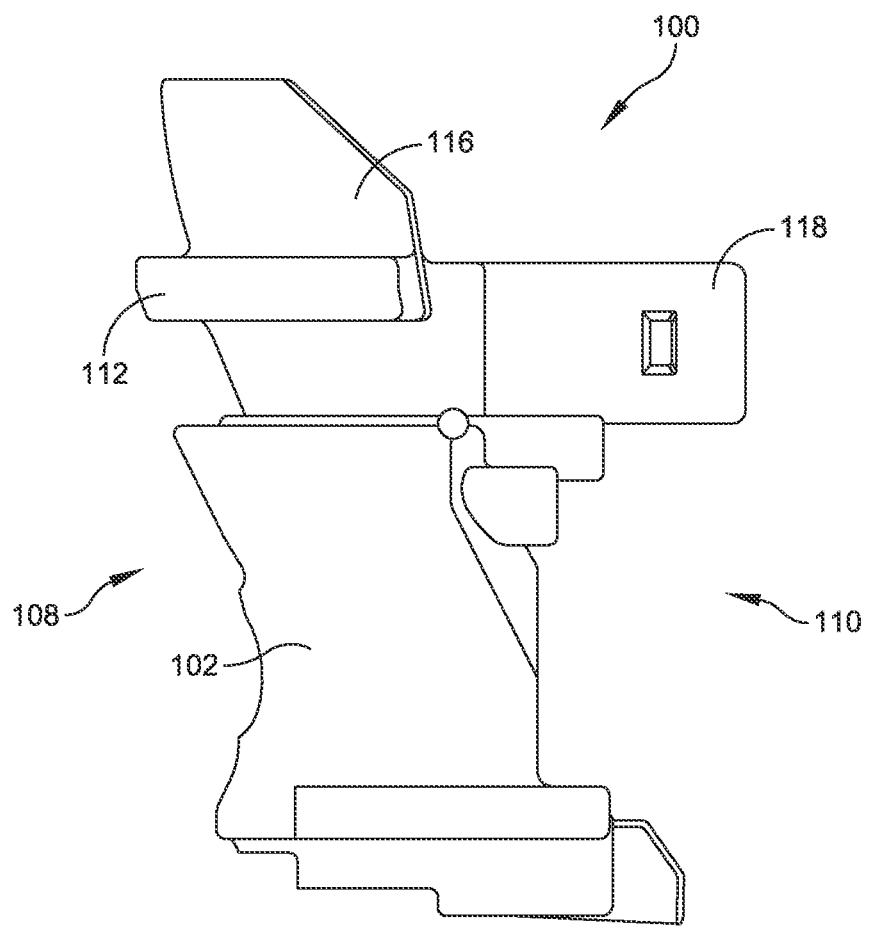
FIG. 3 is a side view of the surgical locator device illustrated in FIG. 2 in accordance with some embodiments.

FIG. 2 illustrates one example of a surgical locator device 100 in accordance with some embodiments. Locator device 100 includes a monolithic body 102 comprising a superior portion 104 and an inferior portion 106. In some embodiments, portions 104 and 106 each respectively include approximately half of body 102 as divided about an approximate midline. However, one of ordinary skill in the art will understand that portions 104 and 106 can be otherwise divided such that inferior portion includes more or less than half of body 102. Body 102 further includes a first side 108 and a second side 110 disposed opposite first 108 as best seen in FIG. 3. In some embodiments, first side 108 is a patient-engaging side and side 110 is configured to be engaged or manipulated by a user.

Figure 4:
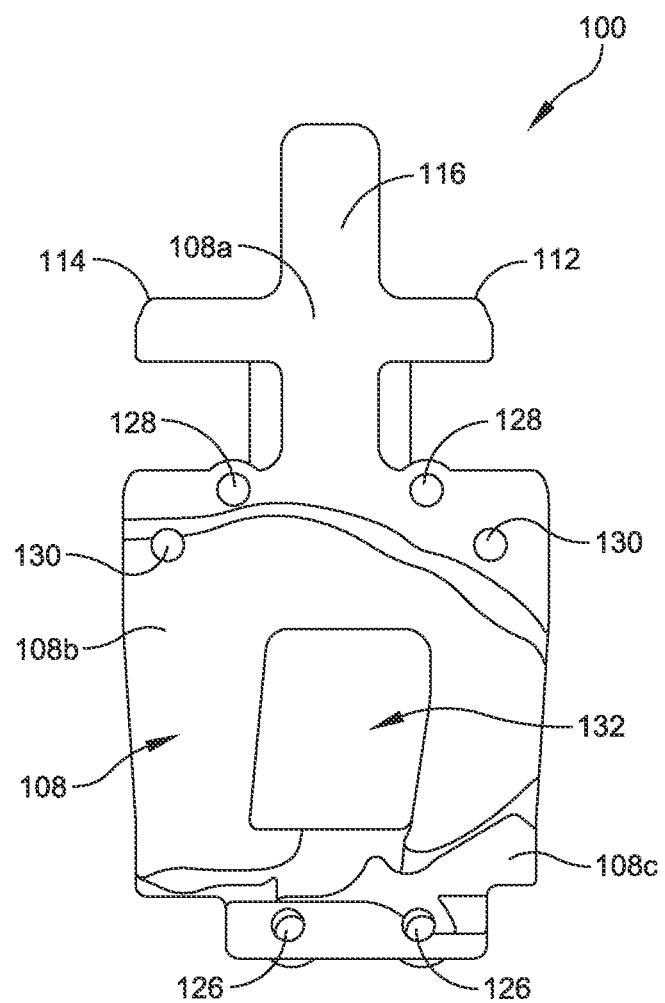
FIG. 4 is a plan view of a patient-engaging side of the surgical locator device illustrated in FIG. 2 in accordance with some embodiments.
Figure 5:
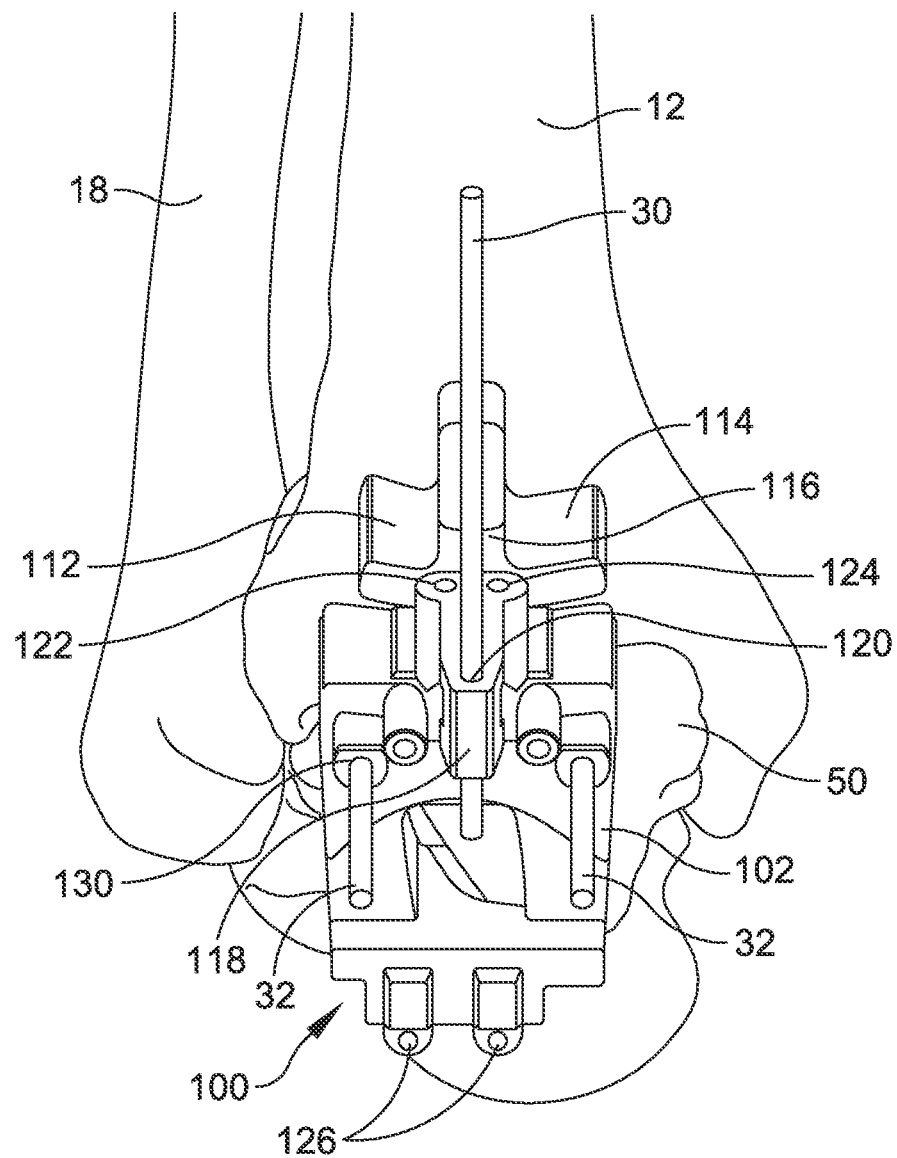
FIG. 5 illustrates one example of a surgical locator device engaging a tibia, talus, and a foreign object positioned between the tibia and talus in accordance with some embodiments.

In some embodiments, superior portion 104 includes a pair of arms 112, 114 that extend away from a base 116 disposed between arms 112, 114 as best seen in FIGS. 2 and 4. Base 116 includes an outwardly extending tab 118 that defines holes 120, 122, 124 therethrough that extend in a superior-inferior direction as best seen in FIG. 5. Hole 120 is disposed in a first plane, and holes 122, 124 are disposed in a second plane that is spaced apart from the first plane in a posterior direction. Each of holes 120, 122, 124 is sized and configured to receive a k-wire, pin, or other elongate radiopaque object therein for reasons described in greater detail below. In some embodiments, holes 122, 124 are spaced apart from one another such that collectively holes 120, 122, 124 are configured to form a gunsight.

Referring now to FIGS. 2 and 4, body 102 defines several pairs of holes that extending in an anterior-posterior direction. For example, in some embodiments, a first pair of holes 126 disposed adjacent to an inferior edge of body 102. The location of hole pair 126 relative to body 102 is determined based on preoperative imaging and planning such that holes are configured to guide the insertion of k-wires, pins, or other elongate surgical instrument into talus 14 is at a specific location that corresponds to the location of holes 2104, 2106 of talar resection guide base 2100 as disclosed in commonly assigned U.S. patent application Ser. No. 14/445,928, entitled "Ankle Replacement System and Method," the entirety of which is incorporated by reference herein, as described in greater detail below. One of ordinary skill in the art will understand that the pair of holes 126 defined by body 102 can facilitate the accurate placement of other cutting guides beyond a talar resection guide base. Further, one of ordinary skill in the art will understand that the number of holes may be varied such that fewer than two (e.g., one) or more holes can be provided for guiding an elongate surgical device (e.g., a pin) into a bone and/or foreign object that is then used to guide another surgical instrument, such as a cutting guide, a drill guide, or a cannulated reamer, to list only a few possibilities.

Hole pair 128 is positioned superiorly relative to hole pair 126. The location of hole pair 128 relative to body 102, in some embodiments, also is determined based on preoperative planning using imaging of the patient such that k-wire(s), pin(s), or other elongate surgical instrument(s) is/are inserted at a location that facilitates the placement of a surgical cutting device on the tibia 12. For example, holes 128 can facilitate the placement of a tibial cutting guide such as cut guide 290 disclosed in commonly assigned U.S. patent application Ser. No. 14/445,928, entitled "Ankle Replacement System and Method." One of ordinary skill in the art will understand that holes 126 defined by body 102 can facilitate the accurate placement of other cutting guides, drill guides, or other surgical instruments. Body 102 defines another pair of holes 130, which are located along body 102 between holes 126 and holes 128. Holes 130 are sized and configured to receive a k-wire, pin, or other elongate surgical device therein for securing surgical locator device 100 to the joint 10.

In some embodiments, body 102 also defines an opening 132 between holes 130 and holes 126 as illustrated in FIGS. 2 and 4. Opening 132 is defined by walls 134, 136, 138, 140 and extends through body 102 (FIG. 2). Advantageously, opening 132 provides a user of surgical locator device 100 with a viewing portal such that the user can view the underlying joint structures when surgical locator device 100 is positioned against the bone or cartilaginous structures of the joint 10.

The patient-engaging side 108 of locator device 100 includes one or more contact surfaces that are designed to be complementary to the prominences and concavities of joint 10, including the surface features of tibia 12, talus 16, and foreign object 50. For example and as best seen in FIG. 4, the superior portion 104 of patient-engaging side 108 of body 102 has a first surface topography 108*a* that is complementary to a distal portion of tibia 12 and, in some embodiments, a second surface topography 108*b* that is complementary to a portion of foreign object 50. Inferior portion 106 of patient-engaging side 108 of body 102 has a third surface topography 108*c* that is complementary to a portion of the talar dome or proximal portion of talus and a portion of foreign object 50.

Figure 11:
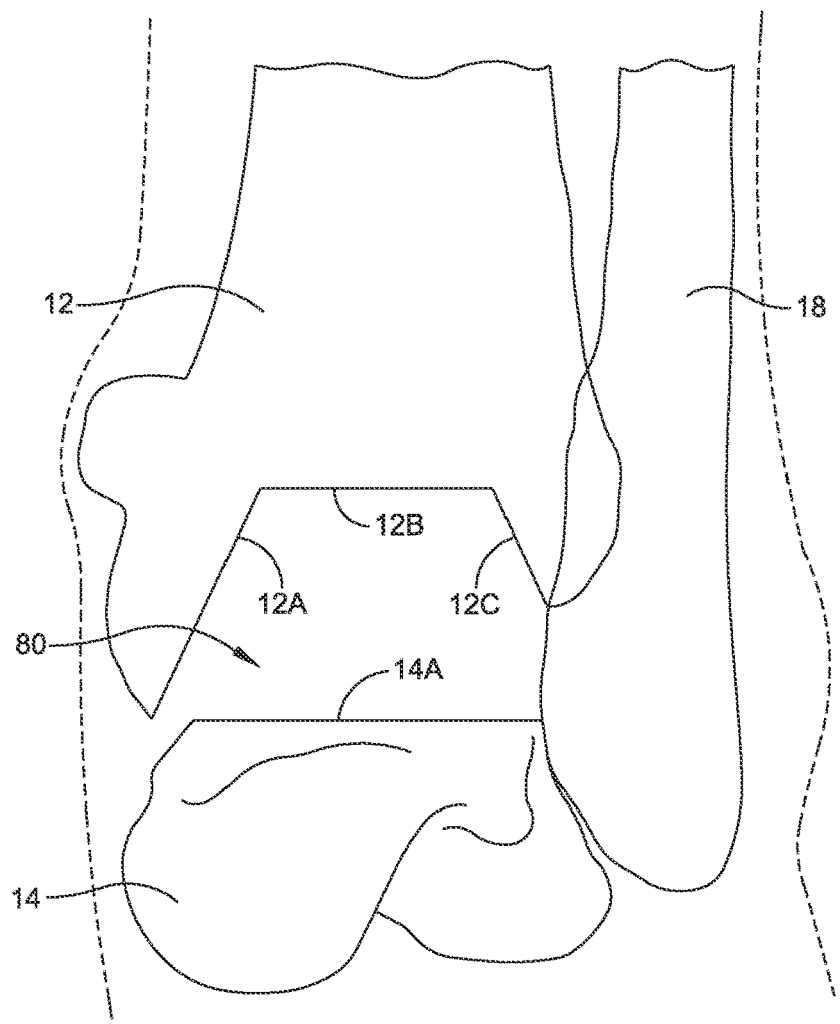
FIG. 11 illustrates one example of a resected bone space created using cutting guides in accordance with some embodiments.
Figure 12:
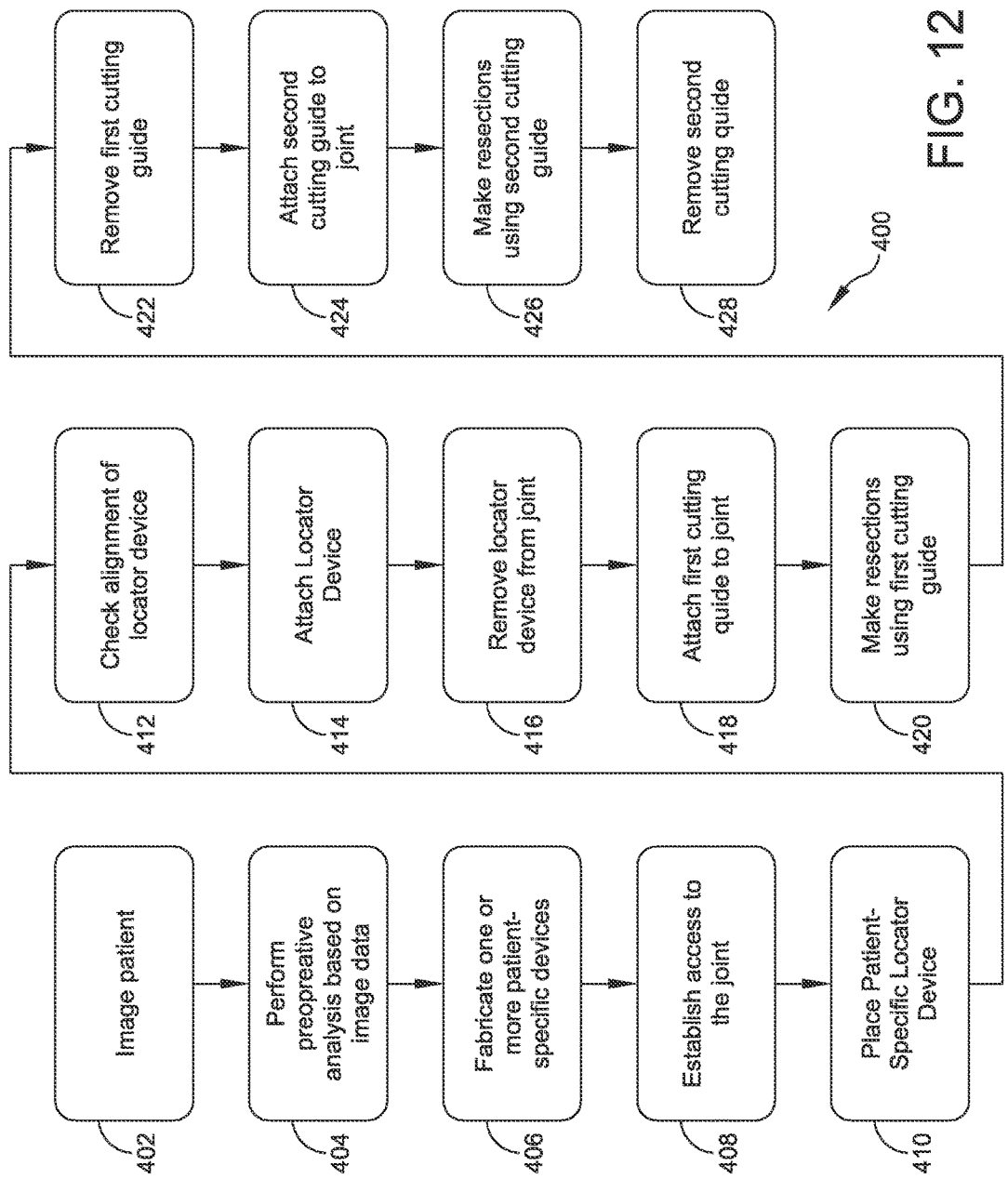
FIG. 12 is a flow diagram of one example of a method in accordance with some embodiments.

The surgical locator devices and systems disclosed herein can be used in a wide variety of surgical methods, including revision surgeries and fusion takedowns to identify only a couple of non-limiting possibilities. One example of a fusion takedown procedure is described now with reference to FIGS. 5-12 in which FIG. 12 is a flow chart of example of a method 400 in accordance with some embodiments. One of ordinary skill in the art will understand that various surgical procedures can be performed using the locator devices disclosed herein and therefore one or more steps of method 400 may be omitted and additional steps also can be performed.

At block 402, the patient is imaged. For example, one or more areas of a patient can be imaged using one or more medical imaging technologies such as x-ray, CT, and/or MRI to list only a few possibilities. In some embodiments, a single joint of the patient is imaged. For example, when the fusion takedown is to be performed on a patient's ankle, one or more images of the patient's ankle can be acquired using medical imaging instrumentation as will be understood by one of ordinary skill in the art.

However, in some embodiments, multiple joints of a patient are imaged in order to gather data concerning the patient's anatomy. For example, in order to be able to determine the anatomical and mechanical axes of the patient's leg, the patient's ankle and at least one other joint, e.g., knee or hip, also will be imaged.

At block 404, the image data is used to perform preoperative analysis of the surgical procedure. For example, the image data is used to generate three-dimensional (3D) renderings of the patient's anatomy, which is then used by a physician to assess the implant site and the develop a surgical plan as described in commonly assigned U.S. patent application Ser. No. 12/711,307, which is incorporated by reference herein. The acquired image data not only includes data concerning the patient's anatomy, such as bones and/or cartilage, but the acquired image data also includes data concerning any foreign objects 50 within the patient's body. The geometry and location of foreign objects 50 within the patient's body is used when developing the surgical plan and preoperative analysis. In some embodiments, foreign object 50 is bone cement used to fuse the ankle joint 10 of the patient. However, one of ordinary skill in the art will understand that foreign object 50 can be an orthopedic implant.

At block 406, one or more patient-specific surgical devices, such as a surgical locator device 100, are fabricated. In some embodiments, a surgical locator device 100 is fabricated using stereolithography or selective laser sintering, to list only a couple of possible examples. The fabricated surgical locator device 100 will be sterilized and prepared for use during surgery as will be understood by one of ordinary skill in the art.

At block 408, access to the joint is established, such as by making an incision to expose the bony and/or cartilaginous surfaces of the joint. In some embodiments, the incision is made along the anterior of the patient's ankle joint 10 to expose at least the tibia 12, talus 14, and foreign object 50.

At block 410, with the joint 10 exposed, the patient-engaging side 108 of surgical locator device 100 is placed in contact with a bony surface, a cartilaginous surface, and/or in contact with a surface of foreign object 50. The position of patient-engaging side 108 relative to the surface of joint 10 is adjusted by the surgeon until the surgical locator device 100 "locks" to joint 10. As will be understood by one of ordinary skill in the art, the "locking" of surgical locator device 100 to joint 10 is accomplished by aligning the complementary prominences and concavities of the patient-engaging side 108 of surgical locator device 100 to the corresponding prominences and concavities of the tibia 12, talus 14, and foreign object 50.

Figure 6:
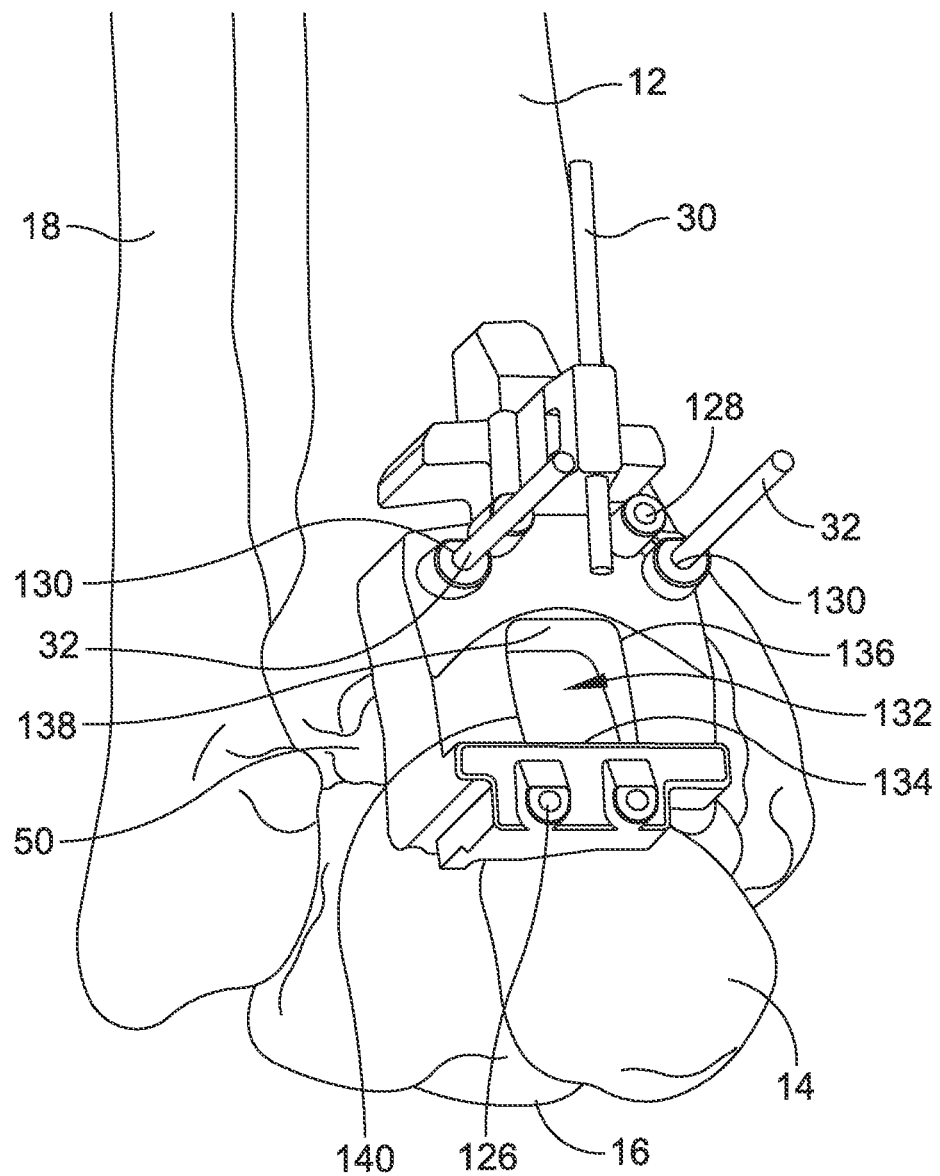
FIG. 6 is another view of the surgical locator device engaging a tibia, talus, and a foreign object positioned between the tibia and talus in accordance with some embodiments.

At block 412, the alignment of surgical locator device 100 relative to tibia 12 is checked. For example, a radiopaque elongate orthopedic device 30 is inserted into hole 120 such that device 30 extends superiorly from base 116 and/or tab 118 of body 102 as shown in FIGS. 5 and 6. In some embodiments, body 102 is pinned to joint 10 by inserting a k-wire or pin 32 into each of holes 130 to secure surgical locator device 100 to joint 10 during a fluoroscopic check. The fluoroscopic check is performed once the surgical locator device 100 is locked to the joint 10 by imaging surgical locator device 100 to confirm the alignment of orthopedic device 100 relative to tibia 12 and/or by checking the gunsight formed by the radiopaque objects disposed within holes 120, 122, 124. The location of surgical alignment device 100 relative to joint 10 can be adjusted intraoperatively by the surgeon depending on the intraoperative fluoro checks. One of ordinary skill in the art will understand that checking the alignment of a surgical locator device relative to an anatomical structure of the patient or with respect to foreign object 50 does not always need to be performed.

At block 414, with the position of locator device 100 relative to joint 10 confirmed, additional k-wires or pins 34, 36 are inserted into the tibia 12 and talus 14 through holes 126 and 128, respectively. For example, a pair of k-wires or pins 34 are inserted into talus 14 by being guided by holes 126 to position the k-wires or pins 34 at a specific location in talus 14. Another pair of k-wires or pins 36 are inserted into tibia 12 by being guided by holes 128 at a specific location in tibia 12.

At block 416, the locator device 100 is removed from its engagement with joint 10. For example, with k-wires or pins 36, 34 received within tibia 12 and talus 14, the k-wires or pins 32 received in holes 130 are removed and body 102 of locator device 100 is slid over the k-wires or pins 34, 36 received within holes 126 and 128 such that a pair of k-wires or pins 36 remain positioned within tibia 12 and another pair of k-wires or pins 34 remain positioned within talus 14.

In some embodiments, the locator device 100 is not removed from its engagement with joint 10. For example, locator device 100 can be configured to include a pre-attached cutting or drill guide such that the pre-attached cutting or drill guide is positioned in the desired location relative to an anatomical structure of the patient or with respect to the foreign object 50 when locator device 10 is positioned. Additionally or alternatively, other surgical tools or devices can be positioned relative to locator device 100 while locator device remains in its engagement with joint 10.

Figure 7:
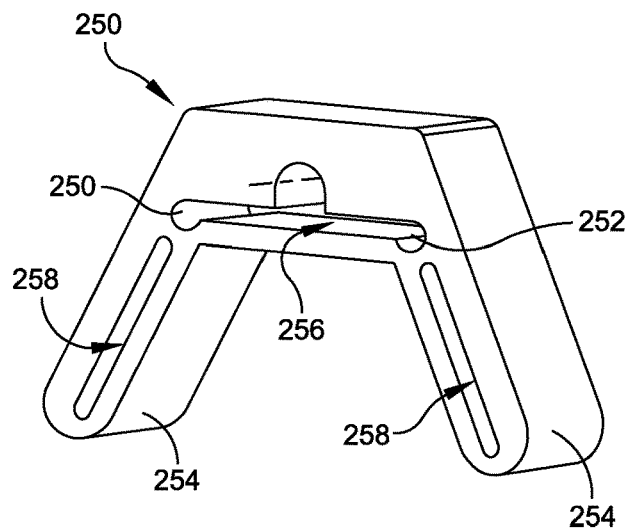
FIG. 7 illustrates one example of a cutting guide that can be positioned using pins placed by a surgical locator device in accordance with some embodiments.
Figure 8:
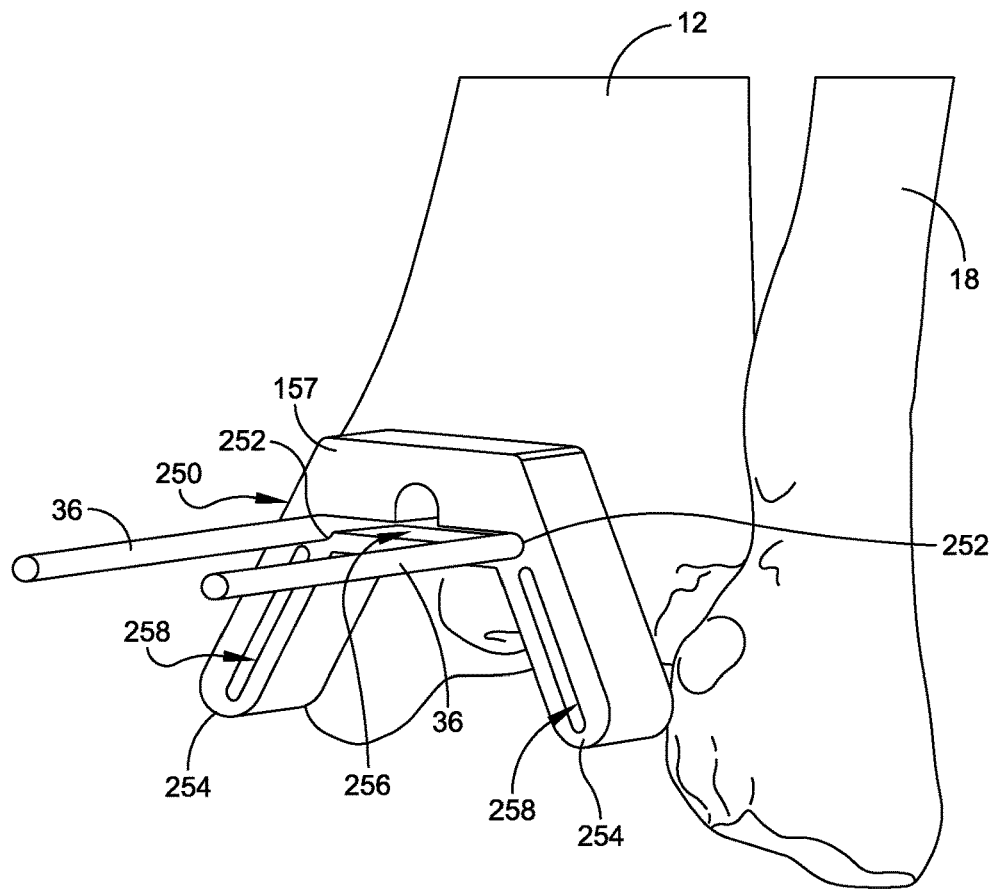
FIG. 8 illustrates the cutting guide illustrated in FIG. 7 positioned against a bone using pins placed by a surgical locator device in accordance with some embodiments.

At block 418, a first cutting guide is attached to one of the pairs of k-wires or pins 34 and/or 36. In some embodiments a tibial cutting guide is positioned relative to tibia 12 by being guided by at least pins 36. For example, and as illustrated in FIG. 7, cutting guide is cutting guide 250. In some embodiments, cutting guide 250 is positioned on tibia 12 by introducing pins 36 into holes 252 defined by cutting guide 250 and sliding cutting guide 250 along pins 36 until it contacts tibia 12 as best seen in FIG. 8.

Figure 9:
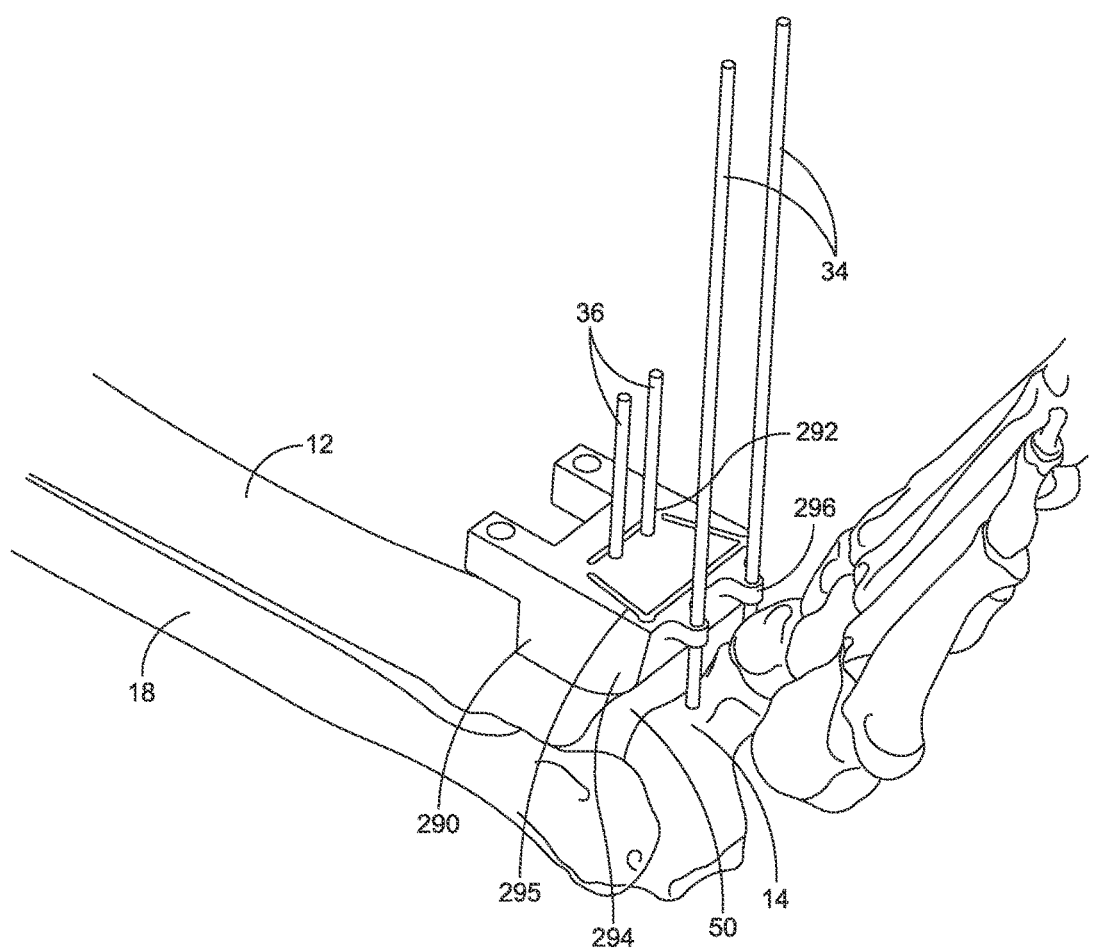
FIG. 9 illustrates one example of another cutting guide being positioned using pins placed by a surgical locator device in accordance with some embodiments.

In some embodiments, the tibial cutting guide takes other forms and engage both pins 34 and 36. One example of such a cutting guide is illustrated in FIG. 9. As shown in FIG. 9, cutting guide 290 is placed relative to tibia 12 and talus 14 by aligning pin holes 292 with pins 36 and aligning pin holes 296 with pins 34. Body 294 of tibial cutting guide 290 is slid along pins 34, 36 until cutting guide 290 contacts tibia 12 and/or talus 14. One of ordinary skill in the art will understand that other cutting guides can be positioned relative to a patient's anatomy by being guided by pins 34 and/or 36 that have been placed using a surgical locator device having a patient-specific surface that is complementary not only to a patient's bony and/or cartilaginous surface, but also to a surface of a foreign body 50 disposed within a patient.

At block 420, resections are made using the first cutting guide. For example, the cutting guide secured to a patient's bone via pins 34 and/or 36 is used to guide a resecting tool, such as a bone saw. In the embodiment illustrated in FIGS. 7 and 8, a saw or other cutting guide is inserted into slot 256 and slots 258, which are defined by arms 254 of cutting guide 250. In the embodiment illustrated in FIG. 9, a bone saw or other cutting device is inserted into slots 294 which guide cutting device as bony cuts are made to the tibia 12. In some embodiments, the cutting guide can be configured such that cuts can be made to both the tibia 12 and talus 14.

In some embodiments the resections made using the first cutting guide includes resecting at least a portion of foreign object 50. For example, foreign object 50 may be positioned within the patient such that when a cutting device is guided by a cutting guide the cutting device makes contact with bone and a portion of foreign object 50.

At block 422, the first cutting guide and supporting pins are removed from the patient. For example, when the first cutting guide is supported by pins 36 as illustrated in FIGS. 7 and 8, pins 36 are removed from their engagement with the tibia 12 and cutting guide 250 also is removed. Pins 34, which do not support a cutting guide in this example, are kept in their position.

Referring now to cutting guide 290 illustrated in FIG. 9, pins 36 are removed from tibia 12, and pins 34 are removed from talus 14. In addition to removing pins and the cutting guides, resected bone and/or resected portions or fragments of foreign object 50 can also be removed from the surgical site as will be understood by one of ordinary skill in the art.

Figure 10:
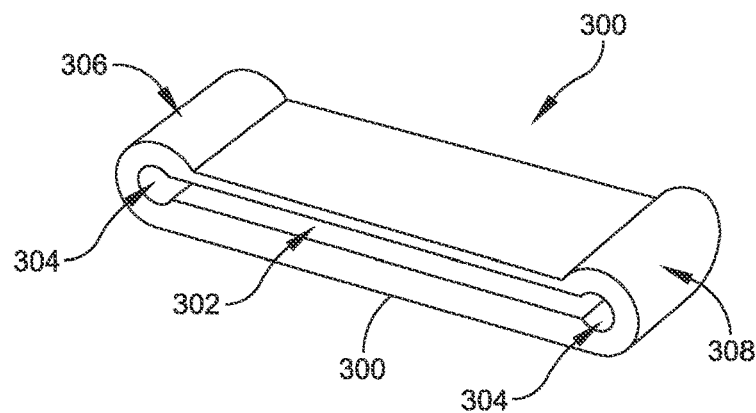
FIG. 10 illustrates another example of another cutting guide configured to be positioned using pins placed by a surgical locator device in accordance with some embodiments.

At block 424, a second cutting guide, if applicable, is attached to a pair of remaining k-wires or pins. For example, FIG. 10 illustrates one example of a talar cutting guide 300 in accordance with some embodiments. Talar cutting guide 300 defines an elongate slot 302 that extends from a first hole 304 defined at a first end 306 to a second hole 306 defined at a second end 308. Cutting guide 300 is positioned by inserting pins 34 extending from talus 14 in holes 304 defined by cutting guide 300 and sliding cutting guide along pins 34 until it contacts talus 14.

At block 426, resections are made using the second cutting guide. For example, the cutting guide secured to a patient's bone via pins 34 is used to guide a resecting tool, such as a bone saw. In the embodiment illustrated in FIG. 10, a saw or other cutting guide is inserted into slot 302 to resect talus 14. In some embodiments the resections made using the second cutting guide 300 includes resecting at least a portion of foreign object 50. For example, foreign object 50 may be positioned within the patient such that when a cutting device is guided by a cutting guide the cutting device makes contact with bone and a portion of foreign object 50.

At block 428, the second cutting guide and supporting pins are removed from the patient, if applicable. For example, pins 34 can be withdrawn from talus 14, and the pins 34 and cutting guide 300 are removed from their engagement with talus 14. As will be understood by one of ordinary skill in the art, the resected bone and/or portion of foreign object 50 also can be removed.

With the resections having been made to the bone and/or foreign object, a void is provided between the bones of the joint for further preparation of the bones and/or foreign object to receive a prosthesis. For example, FIG. 11 illustrates one example of a resected bone space 80 defined by resected surfaces 12A, 12B, 12C of tibia 12, resected surface 14A of talus 14, and femur 18. As shown in FIG. 11, foreign object 50 is not disposed within resected bone space 80 having been removed during the joint resections.

Further surgical steps can be performed to implant a joint prosthesis as will be understood by one of ordinary skill in the art. Examples of such procedures are shown and described in commonly assigned U.S. Pat. Nos. 8,808,297; 8,808,303; and U.S. patent application Ser. No. 14/445,928, all of which are incorporated by reference herein in their entireties. These surgical procedures are only a few examples of possible surgical techniques that can be performed using the patient-specific tools described herein.

The disclosed systems and methods described above advantageously utilize medical imaging to create custom surgical tools that include surfaces that are not only complementary to a patient's bone and/or cartilaginous surface, but also to any foreign objects within the patient. These surgical tools improve the accuracy of performing revision surgeries as well as orthopedic procedures such as fusion takedowns.

In some embodiments, a surgical device includes a body having a first side having a first surface that is complementary to a surface of a foreign object disposed within a patient based on preoperative imaging of the patient. The body defines at least one first hole positioned relative to the body to facilitate insertion of an elongate device at a predetermined location relative to the foreign object.

In some embodiments, the first side includes a second surface that is complementary to at least one of a first bone or a first cartilaginous surface of the patient.

In some embodiments, the first side of the body includes a third surface that is complementary to at least one of a second bone or a second cartilaginous surface of the patient.

In some embodiments, the at least one first bone is different from the at least one second bone.

In some embodiments, the at least one first bone and the at least one second bone together define at least a portion of a joint such that the body is sized and configured to extend across at least the portion of the joint.

In some embodiments, the at least one hole includes a first pair of holes, and the body defines a second pair of holes disposed at a distance from the first pair of holes. The second pair of holes is positioned relative to the body to facilitate insertion of a second pair of elongate devices at a second predetermined location in at least one of the second bone, the second cartilaginous surface, or the foreign object.

In some embodiments, the first pair of holes are defined by a superior portion of the body, and the second pair of holes are defined by an inferior portion of the body.

In some embodiments, the body defines an opening located between the first pair of holes and the second pair of holes.

In some embodiments, a second side of the body includes a tab outwardly extending from a base. The tab defines a hole therein sized and configured to receive a radiopaque object therein.

In some embodiments, a system includes a surgical locator device and a first guide. The surgical locator device including a body having a first side and a second side. The first side of the surgical locator device including a first surface that is complementary to a surface of a foreign object disposed within a patient based on preoperative imaging of the patient. The body defines at least one first hole positioned relative to the body to facilitate insertion of a first elongate device at a predetermined location relative to the foreign object. The first guide defines at least one second hole sized and configured to receive the first elongate device therein for locating the first guide relative to the foreign object.

In some embodiments, the first side includes a second surface that is complementary to at least one of a first bone or a first cartilaginous surface of the patient.

In some embodiments, the first side of the body of the surgical locator device includes a third surface that is complementary to at least one of a second bone or a second cartilaginous surface of the patient.

In some embodiments, the at least one first bone and the at least one second bone together define at least a portion of a joint such that the body of the surgical locator device is sized and configured to extend across at least the portion of the joint.

In some embodiments, the at least one first hole includes a first part of holes, the at least one second hole includes a second pair of holes, and the body of the surgical locator device defines a third pair of holes disposed at a distance from the first pair of holes. The third pair of holes is positioned relative to the body of the surgical locator device to facilitate insertion of a second pair of elongate devices at a second predetermined location in at least one of the second bone, the second cartilaginous surface, or the foreign object.

In some embodiments, a second guide defines a fourth pair of holes that are sized and configured to receive the second pair of elongate devices therein for locating the second guide relative to at least one of the second bone, the second cartilaginous surface, or the foreign object.

In some embodiments, the first pair of holes is defined by a superior portion of the body of the surgical locator device, and the third pair of holes are defined by an inferior portion of the body of the surgical locator device.

In some embodiments, the body of the surgical locator device defines an opening located between the first pair of holes and the third pair of holes.

In some embodiments, a second side of the body includes a tab outwardly extending from a base. The tab defines a hole therein sized and configured to receive a radiopaque object therein.

In some embodiments, a method includes establishing access to a joint of a patient and placing a surgical locator device in contact with the joint such that a first surface of the surgical locator device contacts at least a portion of a foreign object disposed within the patient. The first surface of the surgical locator device is complementary to the portion of the foreign object based on preoperative imaging of the patient.

In some embodiments, a method includes inserting a first pin into a first hole defined by the surgical locator device, removing the surgical locator device from its engagement with the joint of the patient, and sliding a second surgical device along the first pin to locate the second surgical device relative to the joint of the patient.

In some embodiments, placing the surgical locator device in contact with the joint includes placing a second surface of the surgical locator device in contact with at least one of a portion of a first bone or a first cartilaginous surface and placing a third surface of the surgical locator device in contact with at least one of a portion of a second bone or a second cartilaginous surface of a second bone of the joint. The second surface of the surgical locator device being complementary to the at least one of the portion of the first bone and the first cartilaginous surface based on preoperative imaging of the patient. The third surface of the surgical locator device is complementary to at least one of the portion of the second bone or the second cartilaginous surface based on preoperative imaging of the patient.

In some embodiments, a method includes inserting a third pin into a third hole defined by the surgical locator device, inserting a fourth pin into a fourth hole defined by the surgical locator device, and sliding a third surgical device along the third and fourth pins to locate the third surgical device relative to the joint of the patient.

It is to be understood that the disclosed systems and methods are by no means limited only to the particular constructions herein disclosed and shown in the drawings, but also comprises any modifications or equivalents within the scope of the claims.

What is claimed is:

1. A surgical device, comprising:
a body having a first side including a first surface that is complementary to a surface of a foreign object disposed within a patient during preoperative imaging of the patient, wherein the complementary surface is based on the preoperative imaging of the patient, wherein the first side of the body includes (i) a second surface that is complementary to at least one of a first bone or a first cartilaginous surface of the patient and (ii) a third surface that is complementary to at least one of a second bone or a second cartilaginous surface of the patient,
wherein the body defines at least one hole positioned relative to the body to facilitate insertion of an elongate device at a predetermined location relative to the foreign object, and wherein the elongate device is configured to position a cutting guide relative to the foreign object such that a cut formed using the cutting guide removes at least a portion of the foreign object.

2. The surgical device of claim 1, wherein the at least one first bone is different from the at least one second bone.

3. The surgical device of claim 2, wherein the at least one first bone and the at least one second bone together define at least a portion of a joint such that the body is sized and configured to extend across at least the portion of the joint.

4. The surgical device of claim 1, wherein the at least one hole includes a first pair of holes, and wherein the body defines a second pair of holes disposed at a distance from the first pair of holes, the second pair of holes positioned relative to the body to facilitate insertion of a second pair of elongate devices at a second predetermined location in at least one of the second bone, the second cartilaginous surface, or the foreign object.

5. The surgical device of claim 4, wherein the first pair of holes is defined by a superior portion of the body, and the second pair of holes are defined by an inferior portion of the body.

6. The surgical device of claim 5, wherein the body defines an opening located between the first pair of holes and the second pair of holes.

7. The surgical device of claim 1, wherein a second side of the body includes a tab outwardly extending from a base, the tab defining a hole therein sized and configured to receive a radiopaque object therein.

8. A system comprising:
a surgical locator device, the surgical locator device including a body having a first side and a second side, the first side including a first surface that is complementary to a surface of a foreign object disposed within a patient during preoperative imaging of the patient, wherein the complementary surface is based on preoperative imaging of the patient, the first side of the body including (i) a second surface that is complementary to at least one of a first bone or a first cartilaginous surface of the patient and (ii) a third surface that is complementary to at least one of a second bone or a second cartilaginous surface of the patient,
wherein the body defines at least one hole positioned relative to the body to facilitate insertion of a first elongate device relative to the foreign object; and
a first guide defining at least one second hole sized and configured to receive the first elongate device therein for locating the first guide relative to the foreign object, wherein the elongate device is configured to position the first guide relative to the foreign object such that a cut formed using the first guide removes at least a portion of the foreign object.

9. The system of claim 8, wherein the at least one first bone and the at least one second bone together define at least a portion of a joint such that the body of the surgical locator device is sized and configured to extend across at least the portion of the joint.

10. The system of claim 9, wherein the at least one first hole includes a first pair of holes and the at least one second hole includes a second pair of holes, and the body of the surgical locator device defines a third pair of holes disposed at a distance from the first pair of holes, the third pair of holes positioned relative to the body of the surgical locator device to facilitate insertion of a second pair of elongate devices at a second predetermined location in at least one of the second bone, the second cartilaginous surface, or the foreign object.

11. The system of claim 10, further comprising a second guide defining a fourth pair of holes that are sized and configured to receive the second pair of elongate devices therein for locating the second guide relative to at least one of the second bone, the second cartilaginous surface, or the foreign object.

12. The system of claim 10, wherein the first pair of holes is defined by a superior portion of the body of the surgical locator device, and the third pair of holes are defined by an inferior portion of the body of the surgical locator device.

13. The system of claim 12, wherein the body of the surgical locator device defines an opening located between the first pair of holes and the third pair of holes.

14. The system of claim 8, wherein a second side of the body includes a tab outwardly extending from a base, the tab defining a hole therein sized and configured to receive a radiopaque object therein.

15. A method, comprising:
establishing access to a joint of a patient;
placing a surgical locator device in contact with the joint such that a first surface of the surgical locator device contacts at least a portion of a foreign object disposed within the patient during preoperative imaging of the patient,
wherein the first surface of the surgical locator device is complementary to the portion of the foreign object based on the preoperative imaging of the patient:
inserting a first pin into a first hole defined by the surgical locator device;
removing the surgical locator device from its engagement with the joint of the patient; and
sliding a second surgical device along the first pin to locate the second surgical device relative to the joint of the patient, wherein the first pin positions the second surgical device relative to the foreign object such that a cut formed using the second surgical device removes at least a portion of the foreign object.

16. A method, comprising:
establishing access to a joint of a patient; and
placing a surgical locator device in contact with the joint such that a first surface of the surgical locator device contacts at least a portion of a foreign object disposed within the patient during preoperative imaging of the patient,
wherein the first surface of the surgical locator device is complementary to the portion of the foreign object based on the preoperative imaging of the patient; and
wherein placing the surgical locator device in contact with the joint includes:

placing a second surface of the surgical locator device in contact with at least one of a portion of a first bone or a first cartilaginous surface, the second surface of the surgical locator device being complementary to the at least one of the portion of the first bone or the first cartilaginous surface based on preoperative imaging of the patient; and placing a third surface of the surgical locator device in contact with at least one of a portion of a second bone or a second cartilaginous surface of a second bone of the joint, the third surface of the surgical locator device being complementary to at least one of the portion of the second bone or the second cartilaginous surface based on preoperative imaging of the patient.

* * * * *